US 8,901,336 B2

(12) United States Patent
Hong et al.

(10) Patent No.: US 8,901,336 B2
(45) Date of Patent: Dec. 2, 2014

(54) CATALYSTS, METHODS OF MAKING CATALYSTS, AND METHODS OF USE

(75) Inventors: Sukwon Hong, Gwangju (KR); Hwi Min Seo, Namyangju-Si (KR); David R. Snead, Boston, MA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 210 days.

(21) Appl. No.: 13/600,277

(22) Filed: Aug. 31, 2012

(65) Prior Publication Data
US 2013/0060056 A1    Mar. 7, 2013

Related U.S. Application Data

(60) Provisional application No. 61/531,222, filed on Sep. 6, 2011.

(51) Int. Cl.
| | |
|---|---|
| *C07F 1/00* | (2006.01) |
| *C07F 15/00* | (2006.01) |
| *C07F 13/00* | (2006.01) |
| *C07C 257/04* | (2006.01) |
| *C07D 221/20* | (2006.01) |
| *C07D 207/06* | (2006.01) |
| *C07D 209/96* | (2006.01) |

(52) U.S. Cl.
CPC .......... *C07C 257/04* (2013.01); *C07D 221/20* (2013.01); *C07D 207/06* (2013.01); *C07D 209/96* (2013.01); *C07C 2101/08* (2013.01); *C07C 2103/74* (2013.01)
USPC .......... 556/116; 556/46; 556/136; 556/140; 264/270; 264/276

(58) Field of Classification Search
USPC .......... 556/46, 116, 136, 140; 564/270, 276
See application file for complete search history.

(56) References Cited

PUBLICATIONS

Yu, I., et al.; Phosphine-Tethered Carbene Ligands: Template Synthesis and Reactivity of Cyclic and Acyclic Functionalized Carbenes; Organometallics 2010, 29, 6065.
Bellemin-Laponnaz, S., et al.; Synthesis of N,O—heterocyclic carbene and coordinationto rhodium(I) and copper(I) Polyhedron 2010, 29, 30.
Linder, R., et al.; Synthesis of Trimethylplatinum(IV) Complexes with N,N—and N,O—Heterocyclic Carbene Ligands and Their Reductive C—C Elimination Reactions; J. Am. Chem. Soc. 2009, 131, 8861.
Cabeza, J. A., et al.; Reactivity of N—Heterocyclic Carbenes with [Ru3(CO)12] and [Os3(CO)12]. Influence of Ligand Volume and Electronic Effects; Organometallics 2008, 27, 211.
Cabeza, J.A., et al.; Activation of two C—H Bonds of NHC N—methyl groups on triosmium and triruthenium carbonly clusters; Dalton Trans. 2008, 1937.
Ruiz, J., et al.; Synthesis of N—Heterocyclic Carbene Complexes of Manganese(I) by Coupling Isocyanide Ligands with Propargylamines and Propargylic Alcohols; Organometallics 2007, 26, 5687.
Ruiz, J., et al.; Generation of N—Heterocyclic Carbenes by Metal-Mediated Coupling of Propargylamine and Isocyanides; J. Am. Chem. Soc. 2005, 127, 8584.
Hahn, F. E., et al.; Synthesis of Heterobimetallic Metal Derivatives: a Carbene Complexe as Chelate Ligand; Anorg. Allg. Chem. 2003, 629, 1316.

(Continued)

*Primary Examiner* — Porfirio Nazario Gonzalez
(74) *Attorney, Agent, or Firm* — Thomas Horstemeyer, LLP

(57) ABSTRACT

Embodiments of the present disclosure provide for catalysts such as those shown in FIG. 1.1 and in the Examples, methods of making catalysts, methods of using catalysts, and the like.

18 Claims, 3 Drawing Sheets

Compound A

Compound B

(56) References Cited

PUBLICATIONS

Couture, P., et al.; Chemistry of Cyclic Aminooxycarbenes; Can. J. Chem. 1997, 75, 1281.

Tubaro, C., et al.; A Simple Route to Novel Palladium(II) Catalyst with Oxazolin-2-ylidene Ligands; Organometallics 2005, 24, 4153.

Würtz, S., et al.; Surveying Sterically Demanding N—Heterocyclic Carbene Ligands with Restricted Flexibility for Palladium-Catalyzed Cross-Coupling Reactions; Acc. Chem. Res. 2008, 41, 1523.

Kantchev, E. A. B.; Palladium Complexes of N—Heterocyclic Carbenes as Catalysts for Cross-Coupling Reactions—A Synthetic Chemist's Perspective; Angew. Chem., Int. Ed. 2007, 46, 2768.

Scott, N. M., et al.; Stabilization of Organometallic Species Achieved by the Use of N—Heterocyclic Carbene (NHC) Ligands; Eur. J. Inorg. Chem. 2005, 1815.

Lentz, D., et al.; Reaktionen von Pentacarbony(trifluormethylisocyanid)chrom mit Nucleophilen; Chem. Ber. 1990, 123,751.

Wada, M., et al.; Cationic Carbene Complexes of the (Pentachlorophenyl) nickel(II) Moiety and the Spectrochemical Series of Neutral Carbon Ligands; Inorg. Chem. 1979, 18, 417.

Parks, J. E., et al.; Gold Carbene Complexes: Preparation, Oxidation, and Ligand Displacement; J. Organomet. Chem. 1974, 71, 453.

Minghetti, G., et al.; Bis(carbene) complexes of gold(I) and gold(III); J. Organomet. Chem. 1973, 54, C62.

Bonati, F., et al.; New Isocyanide Complexes of Platinum(II); J. Organomet. Chem. 1970, 24, 251.

Crociani, B., et al.; Synthesis and Reactivity of Novel Palladium(II)—Isocyanide Complexes; Inorg. Chem. 1970, 9, 2021.

Badley, E. M., et al.; The Reactions of Isocyanide Complexes of Platinum(II): a Convenient Route to Carbene Complexes; J. Chem. Soc., Chem. Commun. 1969, 1322.

Fischer, H., et al.; 2-Azoniaallenyliden-Komplexe des Magans—Synthese, Struktur und Reaktivitat; J. Organomet. Chem. 1994, 472, 163.

Huang, L., et al.; Characterization of an Intermediate in the Reaction of a Cationic Carbonyl Complex with Secondary Amine to Give a Carbamoyl Complex; Organometallics 1989, 8, 2065.

Filippou, A. C., et al.; Ubergangsmetall—Carben-Komplexe; J. Organomet. Chem. 1987, 329, 223.

Fisher, E. O., et al.; Vierfach koordinierte Carben-Komplexe von Nickel, Kobalt and Eisen; Chem. Ber. 1972, 105, 588.

Alder, R. W., et al.; Stabel Aminooxy—and Aminothiocarbenes; J. Am. Chem. Soc. 1998, 120, 11526.

Conejero, S., et al.; Readily Available Onio-Substituted Methyleneiminium Salts: Single Precursors for a Variety of Aminocarbenes; Angew. Chem., Int. Ed. 2004, 43, 4089.

Merceron-Saffon, N., et al.; Synthesis of Carbenes Through Substitution Reactions at a Carbene Center; Science 2003, 301, 1223.

Eberhard, M. R., et al.; A Simple Building-Block Route to (Phosphanyl-carbene)palladium Complexes via Intermolecular Addition of Functionalized Phosphanes to Isocyanides; Eur. J. Inorg. Chem. 2009, 1313.

Kremzow, D., et al.; Diaminocarbene- and Fischer-Carbene Complexes of Palladium and Nickel by Oxidative Insertion: Preparation, Structure, and Catalytic Activity; Chem.—Eur. J. 2005, 11, 1833.

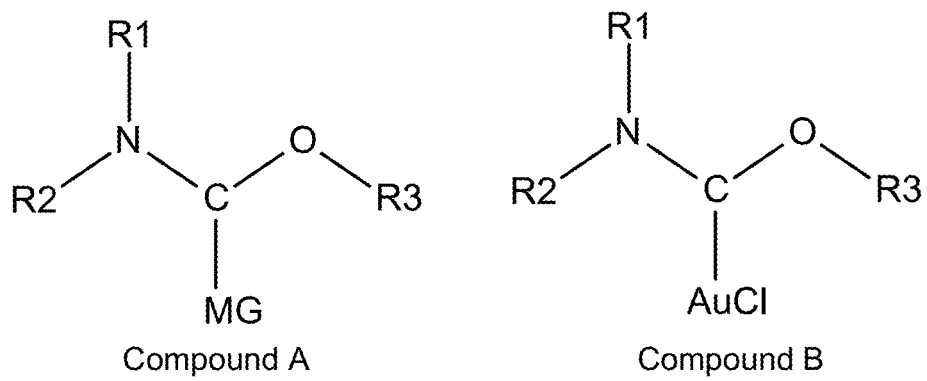
FIG. 1.1
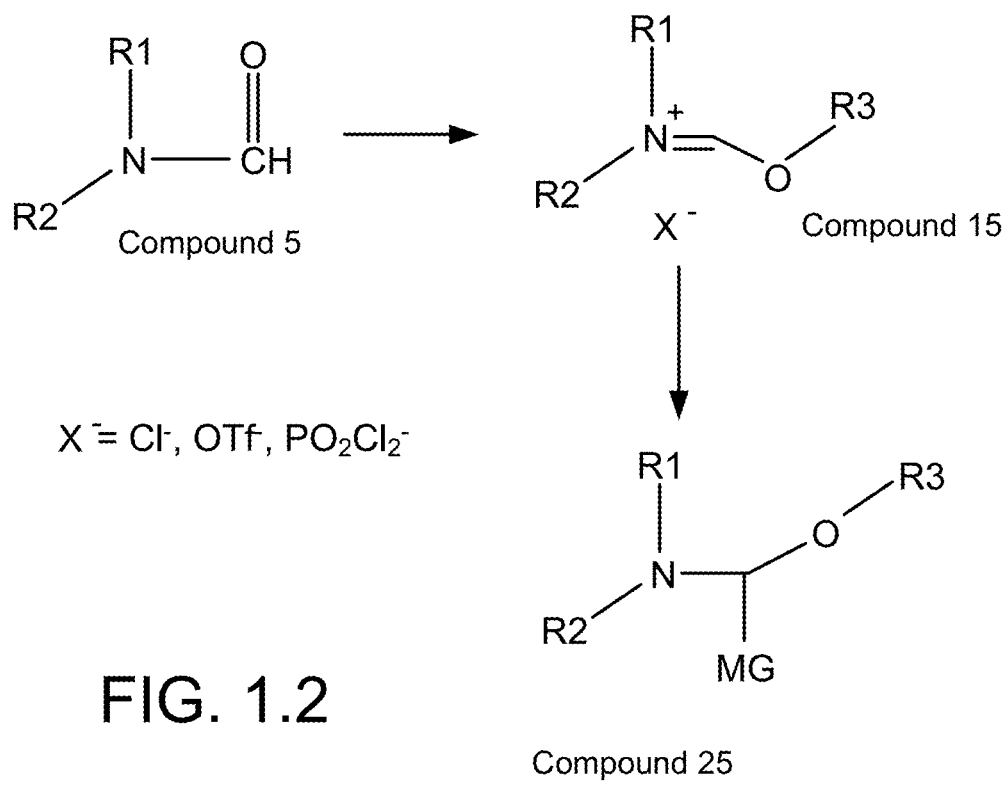
FIG. 1.2

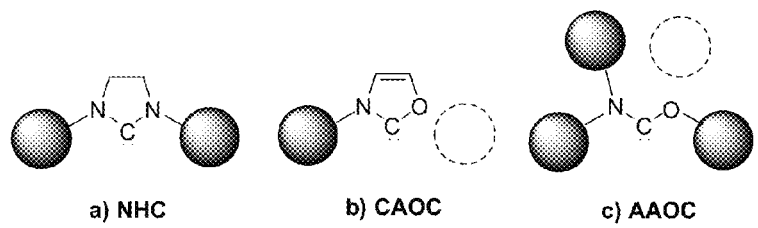
FIG. 2.1
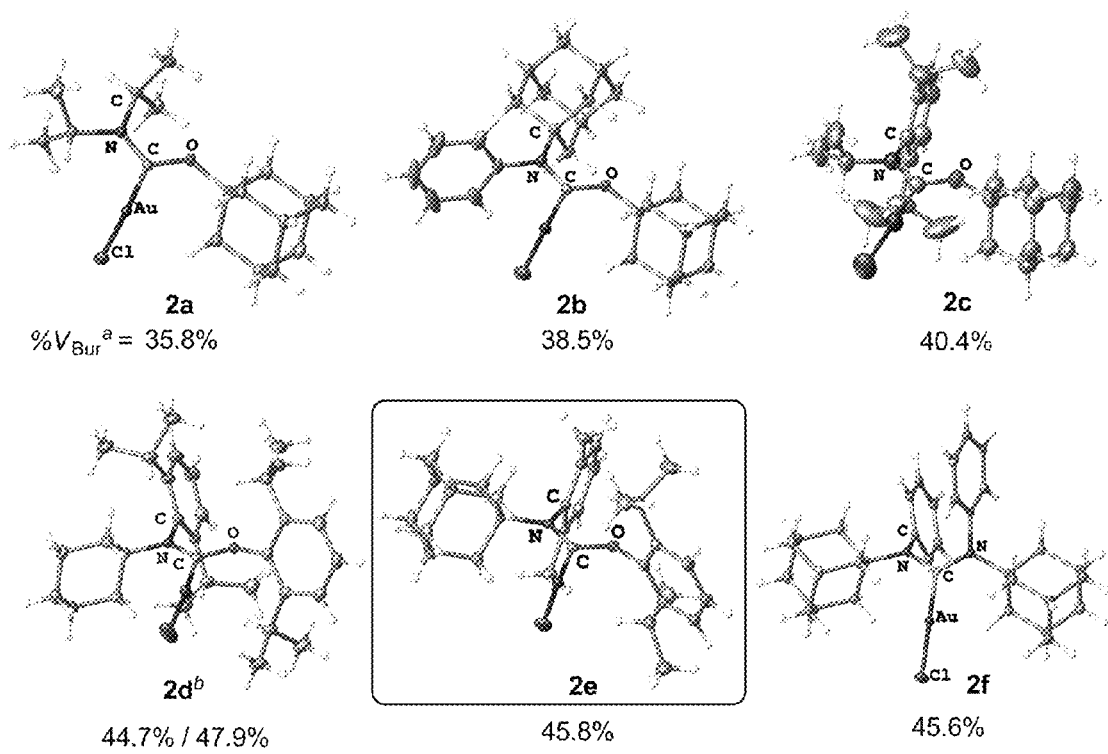
FIG. 2.2

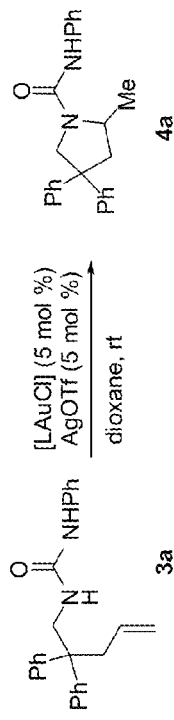
FIG. 2.3
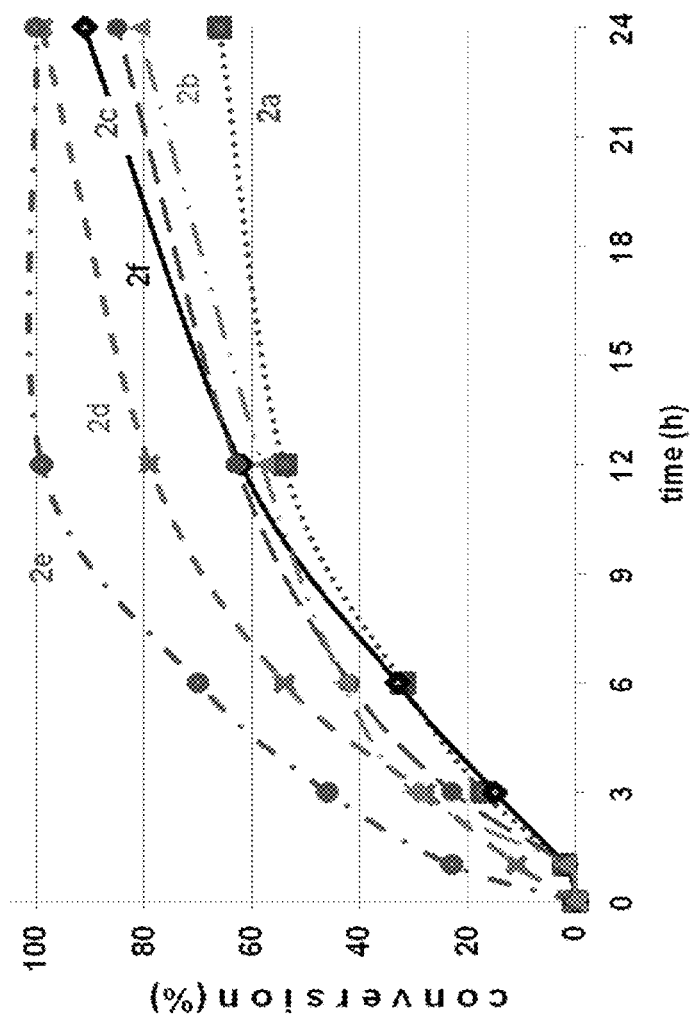
FIG. 2.4

CATALYSTS, METHODS OF MAKING CATALYSTS, AND METHODS OF USE

CROSS-REFERENCE TO RELATED APPLICATION

This application claims priority to U.S. Provisional Application entitled "CATALYSTS, METHODS OF MAKING CATALYSTS, AND METHODS OF USE" having Ser. No. 61/531,222, filed on Sep. 6, 2011, which is incorporated herein by reference.

BACKGROUND

While N-heterocyclic diaminocarbenes (NHCs) have emerged as an important class of ligands in catalysis, their N,O-congeners, cyclic aminooxycarbenes (CAOCs) have not been frequently encountered as ancillary ligands despite having a different electronic profile. The structural variety of CAOCs is rather limited since both bonds of oxygen are incorporated in the heterocyclic core. Furthermore, CAOCs are less bulky than NHCs, because an oxygen lone pair in CAOCs does not exert the same level of steric protection as the flanking N substituents in NHCs. Considering that steric tuning of NHC ligands is often critical in the optimization process and that generally NHC ligands bearing bulky N substituents effectively promote a wide variety of reactions, the inherent lack of such possibilities could be a serious limitation in the potential development of CAOCs as useful ligands. Thus, there is a need to explore other options to overcome these deficiencies.

SUMMARY

Embodiments of the present disclosure provide for catalysts such as those shown in FIG. 1.1 and in the Examples, methods of making catalysts, methods of using catalysts, and the like.

In an embodiment, the compound can include one having the following formula:

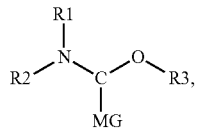

where R1, R2, and R3 are each independently selected from: an unsubstituted or substituted alkyl group, an unsubstituted or substituted cycloalkyl group, and an unsubstituted or substituted aryl group; and MG is a metal group.

In an embodiment, the compound can include one having the following formula:

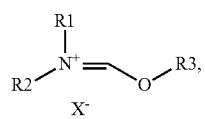

where R1, R2, and R3 are each independently selected from: an unsubstituted or substituted alkyl group, an unsubstituted or substituted cycloalkyl group, and an unsubstituted or substituted aryl group, and X is selected from: Cl, Br, I, $BF_4$, $PF_6$, $BAr_4$, $ClO_4$, OAc, OTf, Ts, Ms, $NTf_2$, and $PO_2Cl_2$.

Other chemicals, composition, systems, methods, features, and advantages of the present disclosure will be or become apparent to one with skill in the art upon examination of the following detailed description. It is intended that all such additional devices, systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 describes catalyst of the present disclosure and these include compound A and compound B.

FIG. 1.2 illustrates a generic scheme for preparing compounds of the present disclosure.

FIG. 2.1 illustrates the steric profiles of diaminocarbenes and aminooxycarbenes.

FIG. 2.2 illustrates a X-ray structures of acyclic aminocarbene-gold(I) complexes.

FIG. 2.3 illustrates an example of Au(I)-catalyzed hydroamination.

FIG. 2.4 illustrates a graph of the reaction profile of Au(I)-catalyzed hydroamination for each of compounds 2a to 2f.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions

The term "substituted" refers to any one or more hydrogens on the designated atom that can be replaced with a selection from the indicated group, provided that the designated atom's normal valence is not exceeded, and that the substitution results in a stable compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "alkynyl" refers to straight or branched chain hydrocarbon groups having 2 to 12 carbon atoms, preferably 2 to 4 carbon atoms, and at least one triple carbon to carbon bond, such as ethynyl. An alkynyl group is optionally substituted, unless stated otherwise, with one or more groups, selected from aryl (including substituted aryl), heteroaryl, heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

To the extent that the disclosed compounds, and salts thereof, may exist in their tautomeric form, all such tautomeric forms are contemplated herein as part of the present disclosure.

All stereoisomers of the compounds of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

Discussion

Embodiments of the present disclosure provide for catalysts such as those shown in FIG. 1.1 and in the Examples, methods of making catalysts, methods of using catalysts, and the like. Catalysts of the present disclosure can be useful in various catalytic transformations. Embodiments of the catalyst can be used in hydroamination, cycloisomerization, allylic rearrangement reactions, alkyne hydration reactions, Meyer-Schuster rearrangement reactions, and the like. Additional details are described in the Example section.

FIG. 1.1 describes catalysts of the present disclosure and these include compound A and compound B. Compound A is a general formula of compounds of the present disclosure, while compound B (MG is AuCl) is a specific embodiment of a type of compound of the present disclosure. Compounds A and B are conformationally stable in that they retain one conformation and do not switch like other compounds during catalysis. Although not intending to be bound by theory, it is postulated that the bulk of the groups (R1, R2, and/or R3) contributes to the conformational stability of compounds A and B. In addition, compounds A and B are sterically demanding in that certain bonds cannot be accessed by S$_N$2 reaction pathways. See the Example section for additional details.

R1, R2, and R3 are each independently selected and can be the same or different. In an embodiment, R1, R2, and R3 can be a bulky group and are sterically demanding. In an embodiment, R1, R2, and R3 cannot be accessed by S$_N$2 reaction pathways.

In an embodiment, R1, R2, and R3 can each be a secondary alkyl group (unsubstituted or substituted), a tertiary alkyl group (unsubstituted or substituted), or an aromatic group (unsubstituted or substituted). In particular, R1, R2, and R3 can be independently selected from one of the following groups: tert-butyl, adamantyl, isopropyl, cyclopentyl, cyclohexyl, cycloheptyl, cyclooctyl, 1-phenylethyl, 1-cyclohexylethyl, 1-(1-naphthyl)ethyl, 1-(tert-butyl)ethyl, 1-(o-methoxyphenyl)ethyl, phenyl (Ph), 2,6-diisopropylphenyl, 2,6-dimethylphenyl, 1-naphthyl, 2-naphthyl, 2-alkylphenyl, 2-alkoxyphenyl, 2-halophenyl, 2-arylphenyl, 4-alkylphenyl, 4-alkoxyphenyl, 4-halophenyl, 4-arylphenyl, 3,5-dialkylphenyl, 3,5-dialkoxyphenyl, 3,5-dihalophenyl, and 3,5-diarylphenyl, any of which can be unsubstituted or substituted. In an embodiment, each of R1, R2, and R3 can be independently selected from adamantyl, isopropyl, cyclohexyl, phenyl, 2,6-diisopropylphenyl, and 2,6-dimethylphenyl.

MG is a metal group. In an embodiment, M can be a metal that can be used in a catalytic reaction. In an embodiment, M can be a metal such as Au, Pt, Ir, Rh, Re, Ru, Ni, Pd, Cu, Fe, and Co. G can be one or more (depending on the charge of the metal ion) halogens, cyanide, alkenes, dienes, alkynes, allyls, alkyls, aryls, alcohols, amines, phosphines, carbonyls, nitriles, isonitriles (isocyanides), isocyanates or a combination thereof. In an embodiment MG can be selected from the following: AuCl, AuCN, Ir(COD)Cl, Rh(COD)Cl, Ir(CO)$_2$Cl and Rh(CO)$_2$Cl. In an embodiment MG can be AuCl.

FIG. 1.2 illustrates a generic scheme for preparing compounds of the present disclosure, where R1, R2, and R3 can each be independently selected from groups mentioned herein. Additional details regarding a specific synthesis scheme are described in the Examples. FIG. 1.2 illustrates that compound 5 is reacted with (COCl)$_2$, trifluoromethanesulfonic anhydride, or phosphoryl chloride in a solvent (e.g., THF, methylene chloride, acetone, chloroform, toluene) for about 1 to 3 hours at about −80° C. to room temperature. Then R3-OSiMe$_3$ is reacted for about 5 to 9 hours at about −80° C. to room temperature to form compound 15. Compound 15 is reacted with LiHMDS (lithium hexamethyldisilazide) or NaHMDS (sodium hexamethyldisilazide) in a solvent (e.g., THF, diethyl ether, or the like) for about 10 to 60 min at about −78° C. to room temperature and then reacted with Me$_2$S.AuCl in a solvent (e.g., THF, diethyl ether, or the like) for about 0.5 to 3 hours at about −78° C. to room temperature to form compound 25.

As noted above, catalysts of the present disclosure can be used in various reactions. A few of the reactions are shown below, where a specific catalyst is used, but other catalysts of the present disclosure can also be used.

Hydroamination

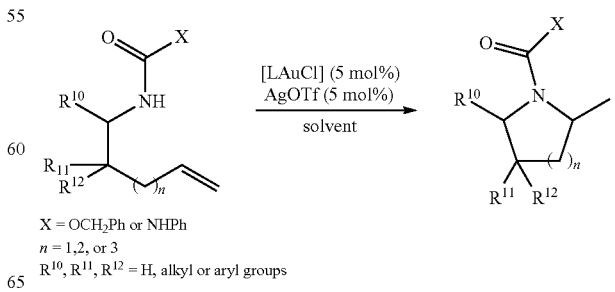

X = OCH$_2$Ph or NHPh
n = 1, 2, or 3
R$^{10}$, R$^{11}$, R$^{12}$ = H, alkyl or aryl groups Cycloisomerization

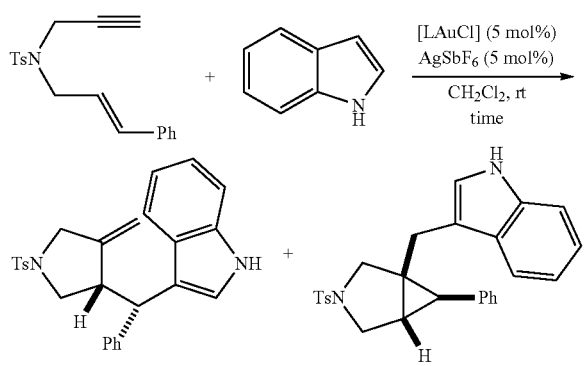

Allylic rearrangement

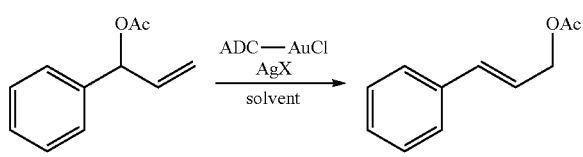

Alkyne hydration, where R13 and R14 can be alkyl groups or aryl groups

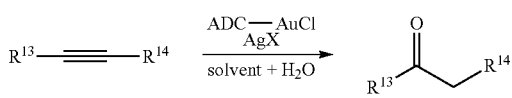

Meyer-Schuster rearrangement, where R15, R16 and R17 can be alkyl groups or aryl groups

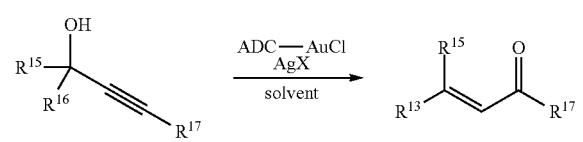

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Brief Introduction

A series of sterically demanding acyclic aminooxycarbenes (AAOCs) were prepared in good yields from chloroiminium salts and alkoxysilanes via the TMS-Cl elimination pathway. The steric profiles of bulky AAOCs were determined by X-ray crystallographic studies of the Au(I)-complexes. The percent buried volume values (% $V_{Bur}$) of the AAOC ligands range from 35.8% to 47.9%. Acyclic aminooxycarbenes maintain coplanarity around the carbene center, in sharp contrast to the similarly bulky acyclic diaminocarbenes that show significant distortion from the coplanarity. The Au(I)-complexes of AAOCs exhibited high efficiency in the hydroamination of alkenyl ureas. Bulkier AAOC-Au(I) complexes displayed faster reaction rates and higher conversions. Reaction rate, yield, and stereoselectivity observed with AAOC-Au(I) catalyst were better than those with acyclic diaminocarbene Au catalysts and comparable to the best results reported to date.

Introduction

While N-heterocyclic diaminocarbenes (NHCs) have emerged as an important class of ligands in catalysis,[1] their N,O-congeners, cyclic aminooxycarbenes (CAOCs) have not been frequently encountered as ancillary ligands despite having a different electronic profile (FIG. 2.1).[2,3] The structural variety of CAOCs is rather limited since both bonds of oxygen are incorporated in the heterocyclic core. Furthermore, CAOCs are less bulky than NHCs, because an oxygen lone pair in CAOCs does not exert the same level of steric protection as the flanking N substituents in NHCs. Considering that steric tuning of NHC ligands is often critical in the optimization process and that generally NHC ligands bearing bulky N substituents are effectively promote a wide variety of reactions,[4] the inherent lack of such possibilities could be a serious limitation in the potential development of CAOCs as useful ligands. We envisioned that acyclic aminooxycarbenes (AAOCs), in contrast, could impose the steric bulk if the nitrogen substituents are large enough to position the oxygen substituent toward the metal center in the preferred conformation (FIG. 2.1c, where FIG. 2.1 illustrates the steric profiles of diaminocarbenes and aminooxycarbenes).

Typically, AAOC-metal complexes have been prepared from addition of alcohols to metal-isocyanide complexes[5] or addition of amines to metal-CO complexes.[6] However, these methods cannot be used to make AAOCs featuring bulky substituents on both oxygen and nitrogen atoms.[7] The free carbenes of sterically demanding AAOCs were developed by the research group of Alder[8] and Bertrand,[9] albeit no catalytic activity was reported. To the best of our knowledge, examples of AAOC-metal catalyzed reactions are rare.[10] In the pursuit of acyclic aminocarbene-metal catalysts,[11] we recently developed highly bulky acyclic diaminocarbenes (ADCs) displaying unique ligand properties in gold catalysis.[11a] Herein, we report the synthesis of bulky AAOC-Au(I) complexes and their remarkable efficiency in the intramolecular hydroamination of alkenyl ureas.

Results and Discussion

Alkoxyiminium salts (1a-e) were prepared from alkoxysilanes and chloroiminiums, following the TMS-Cl elimination protocol that was effective in the synthesis of analogous formamidinium salts[11a] (Scheme 1). Corresponding gold(I)-complexes (2a-e) were then synthesized by deprotonation of the alkoxyiminium salts followed by metalation with Me₂S.AuCl.

Scheme 1. Synthesis of AAOC—Au(I) complexes.

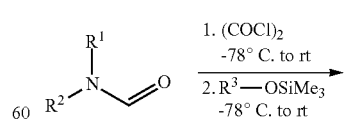

| Compound | R¹ | R² | R³ |
|---|---|---|---|
| 1a/2a | iPr | iPr | Ad |
| 1b/2b | Ad | Ph | Ad |
| 1c/2c | DIPP | iPr | Ad |
| 1d/2d | DIPP | Cy | DIPP |
| 1e/2e | DMP | Ad | DIPP |

-continued

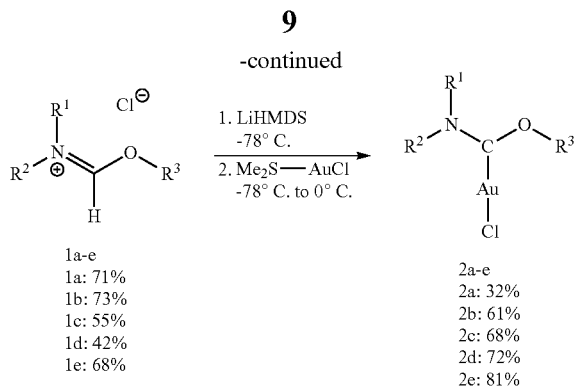

1a-e
1a: 71%
1b: 73%
1c: 55%
1d: 42%
1e: 68%

2a-e
2a: 32%
2b: 61%
2c: 68%
2d: 72%
2e: 81%

Ad = adamantyl, Cy = cyclohexyl, DIPP = 2,6-diisopropylphenyl, DMP = 2,6-dimethylphenyl The three dimensional structure of AAOC-AuCl complexes (2a-e) was characterized by X-ray crystallography, and % buried volume (% $V_{Bur}$)[12] was calculated to compare steric properties of newly prepared AAOC ligands (FIG. 2.2).[13] To our delight, the AAOC ligands in 2d and 2e are highly sterically demanding as the oxygen substituent is oriented proximal to the metal, and their % $V_{Bur}$ values (44.7%/47.9% and 45.8%) are comparable to those of other known bulky diaminocarbenes such as IPr[14] (45.6%) or the $Ph_2Ad_2$-ADC in 2f (45.7%).[11a] The X-ray data also revealed unique structural features of AAOC ligands distinct from the ADCs. In AAOCs the $R^1$ position of the N substituent (which is distal from the metal and proximal to the oxygen lone pair) seems to accommodate the steric bulk better than the $R^2$ position. For example, 2b prefers the adamantyl group at the $R^1$ position (away from the metal), whereas related ADC-AuCl 2f has the adamantyl group toward the metal center. It is interesting to note that in 2c-e the $R^1$ position is preferentially taken by ortho-disubstituted phenyl rings (2,6-diisopropylphenyl or 2,6-dimethylphenyl) over bulky alkyl groups such as isopropyl, cyclohexyl, or adamantyl. In addition, AAOC-AuCl (2a-e) displayed a relatively small dihedral angle of C—N—C—O (ranging from 1.2° to 6.3°), in sharp contrast to ADC-AuCl (2f)[11a] showing significant distortion from the coplanarity (C—N—C—N dihedral angle: 41.0°) (Table 1). AAOCs seem to maintain the coplanarity around the carbene carbon, owing to the fact that there is much less steric interaction between $R^1$ and the oxygen lone pair (or $R^3$).

FIG. 2.2 illustrates a X-ray structures of acyclic aminocarbene-gold(I) complexes. [a]% $V_{Bur}$ values are calculated using X-ray crystallographic data. [b] Two structures found in the crystal unit cell.

Recently ADCs have attracted attention from the synthetic community as alternative ligands in Au-catalysis.[11a,15] New AAOC-Au(I) complexes (2a-e) were tested in Au-catalyzed intramolecular hydroamination of alkenyl ureas since sterically demanding diaminocarbene ligands showed high rates of reaction.[11a,16] FIG. 2.4 illustrates that a similar trend was observed with AAOCs. Thus, faster rates and higher conversions were displayed by the bulkier AAOCs (2e>2d>2a), and it is important to note that highly bulky AAOC-Au catalysts (2d and 2e) exhibited much higher reactivity than the analogous ADC-Au catalyst 2f. Furthermore, less bulky AAOCs (2a-c) also showed noticeable conversions at room temperature,[17] while use of diaminocarbenes (NHCs and ADCs) of similar steric demand (% $V_{Bur}$ less than 40%) resulted in negligible product formation under the same conditions.[11a]

FIG. 2.3 illustrates the reaction profile of Au(I)-catalyzed hydroamination. FIG. 2.4 illustrates the reaction profile of Au(I)-catalyzed hydroamination for each of compounds 2a to 2f. Representative structures of compounds 2a to 2f are shown in FIG. 2.2.

The optimized AAOC-Au catalyst 2e is effective for catalytic hydroamination of various alkenyl ureas (Table 2). With gem-dialkyl substitution, the reaction proceeded smoothly at room temperature to afford 5-membered pyrrolidines (entries 1, 2, 5) and a 6-membered piperidine product (entry 3). The reaction also tolerates more challenging substrates including 2,2-disubstituted alkene substrate (entry 2) and less reactive substrates without gem-dialkyl substituents albeit at higher reaction temperature and catalyst loading (entries 4, 7). It is noteworthy that AAOC-Au catalyst 2e exhibited better yield and improved cis-selectivity compared to ADC-Au catalyst 2f for the formation of 2,3,3,5-tetrasubstituted pyrrolidine 4e (entries 5 vs 6) and 3,5-disubstituted pyrrolidine 4f (entries 7 vs 8). These results are also comparable to those obtained by IPrAuCl, the best gold catalyst for hydroamination of alkenyl ureas known to date.[18]

TABLE 1

Selected bond lengths [Å], angles [°], and torsion angles [°] for 2a-e.

|  | 2a | 2b | 2c | 2d | 2e |
|---|---|---|---|---|---|
| Bond lengths [Å] | | | | | |
| N—$C_{carbene}$ | 1.317(2) | 1.330(2) | 1.336(5) | 1.328(2), 1.314(2) | 1.319(2) |
| O—$C_{carbene}$ | 1.331(2) | 1.325(2) | 1.336(4) | 1.345(2), 1.345(2) | 1.353(2) |
| Au—$C_{carbene}$ | 2.007(2) | 1.996(2) | 2.005(4) | 1.983(2), 1.990(2) | 1.996(1) |
| Au—Cl | 2.2910(5) | 2.2834(6) | 2.287(1) | 2.2883(6), 2.2768(4) | 2.2820(4) |
| Bond angles [°] | | | | | |
| N—$C_{carbene}$—O | 111.5(2) | 112.5(2) | 110.7(3) | 110.7(2), 11.6(2) | 110.9(1) |
| $C_{carbene}$—Au—Cl | 173.45(5) | 178.39(5) | 176.3(1) | 175.13(5), 177.63(6) | 178.41(4) |
| Torsion angles [°] | | | | | |
| C—N—$C_{carbene}$—O | 2.2(3) | 1.3(2) | 6.3(4) | 1.2(2), 3.4(2) | 5.6(2) |

TABLE 2

Hydroamination of alkenyl ureas catalyzed by AAOC-Au(I).[a]

| entry | product | LAuCl | time. temp | yield (%)[b] | cis: trans[c] |
|---|---|---|---|---|---|
| 1[d] | 4a (Ph, Ph, Me, NHPh pyrrolidine carboxamide) | 2e (5 mol %) | 15 h, rt | 98 | N.A |
| 2[e] | 4b (spirocyclohexyl, Me, Me, NHPh) | 2e (5 mol %) | 24 h, rt | 98 | N.A |
| 3[e] | 4c (spirocyclohexyl piperidine, Me, NHPh) | 2e (5 mol %) | 48 h, rt | 94 | N.A |
| 4[d] | 4d (Me, NHBn) | 2e (10 mol %) | 60 h, 45 C. | 86[f] | N.A |
| 5[e] 6[e] | 4e (Ph, Me, Me, NHPh) (2,5-cis/trans) | 2e (5 mol %) 2f (5 mol %) | 24 h, rt 24 h, rt | 98 62[f] | 3.5:1 2.3:1 |
| 7[d] 8[d] | 4f (Ph, Me, NHPh) (3,5-cis/trans) | 2e (10 mol %) 2f (10 mol %) | 30 h, 45° C. 30 h, 45° C. | 98 71[f] | 2.1:1 1.8:1 | a 0.05M conc. [LAuCl] and AgOTf were stirred for 30 min before addition of 3. b Isolated yield. c Determined by 1H NMR. d Dioxane used as a solvent. e Methanol used as a solvent. f Conversion determined by 1H NMR.

Conclusions

Sterically demanding acyclic aminooxycarbenes (AAOCs) and their gold complexes were prepared. X-ray crystallographic studies revealed unique structural features of these bulky AAOC ligands, including coplanarity around the carbene center and the preferential placement of the bulky nitrogen substituent away from the metal. Importantly, one of the most sterically demanding AAOC-Au(I) catalysts (2e) exhibited high efficiency in intramolecular hydroamination of various alkenyl ureas. Reaction rate, yield, and stereoselectivity observed with AAOC-Au(I) catalyst were better than those with acyclic diaminocarbene (ADC) Au catalysts and comparable to the best results reported to date. To the best of our knowledge, this report represents the first example of effective aminooxycarbene ligands used in Au catalysis.

Experimental

General: All reactions were conducted in flame-dried glassware under an inert atmosphere of dry argon. THF, $CH_2Cl_2$, and toluene were purified under a positive pressure of dry nitrogen by Meyer Solvent Dispensing System prior to use. 1,4-Dioxane was dried over Na/benzophenone and was distilled. All the other chemicals used were purchased from Sigma-Aldrich Co., Acros Organics and Strem Chemicals Inc. and were used as received without further purification. NMR spectra were recorded using a Mercury-300 FT-NMR, operating at 300 MHz for $^1H$ NMR and at 75.4 MHz for $^{13}C$ NMR. All chemical shifts for $^1H$ and $^{13}C$ NMR spectroscopy were referenced to residual signals from $CDCl_3$ ($^1H$) 7.27 ppm, ($^{13}C$) 77.23 ppm. High resolution mass spectra were recorded on a Finnigan MAT95Q Hybrid Sector spectrometer or an Agilent 6210 TOF-LC/MS.

1-Adamantanoxydimethylmethanaminium Chloride (1a). Oxalyl chloride (0.85 mL, 10 mmol) was added dropwise to a toluene (15 mL) solution of diisopropylformamide (0.818 g, 6.33 mmol) at −78° C. The solution was stirred for 2 h at room temperature before evaporating all the volatiles in vacuo. $CH_2Cl_2$ (10 mL) was added to the dry mixture, and then S2 (1.46 g, 6.51 mmol) was added at −78° C. After stirring for 3 h at room temperature, the solution was concentrated to 3 mL. The concentrated solution was dropped into vigorously stirred hexanes (20 mL). Washing the precipitated solid with additional hexanes (60 mL) gave 1a as a white solid (1.34 g, 70.5%). $^1H$ NMR (300 MHz, $CDCl_3$) δ 10.22 (s, 1H), 5.20-4.98 (m, 1H), 3.92-3.77 (m, 1H), 2.31 (br. s, 3H), 2.27-2.18 (m, 6H), 1.79-1.53 (m, 6H), 1.39 (d, J=6.8 Hz, 6H), 1.38 (d, J=6.8 Hz, 6H); $^{13}C$ NMR (75 MHz, $CDCl_3$) 165.4, 93.4, 56.9, 49.5, 42.0, 35.2, 31.7, 20.7, 20.0. HRMS-ESI (m/z): [M−Cl]$^+$ calcd for $C_{17}H_{30}NO$, 264.2327; found, 264.2322.

1-Adamantanoxy-N-(1-adamantyl)-N-phenylmethanaminium chloride (1b). With the same method used in the synthesis of 1a, 1b (73.4%) was obtained as a white solid from N-(1-adamantyl)-N-phenylformamide and 1-adamantyloxytrimethylsilane. $^1H$ NMR (300 MHz, $CDCl_3$) δ 9.75 (s, 1H), 7.56-7.42 (m, 3H), 7.16-7.06 (m, 2H), 2.32-2.10 (m, 19H), 1.78-1.53 (m, 11H); $^{13}C$ NMR (75 MHz, $CDCl_3$) δ 165.9, 133.7, 130.2, 129.8, 127.4, 94.9, 66.7, 41.8, 41.6, 35.3, 35.2, 31.8, 30.1. HRMS-ESI (m/z): [M−Cl]$^+$ calcd for $C_{27}H_{36}NO$, 390.2791; found 390.2787.

1-Adamantanoxy-N-(2,6-diisopropylphenyl)-N-isopropylmethanaminium chloride (1c). With the same method used in the synthesis of 1a, 1c (54.5%) was obtained as a white solid from N-(2,6-diisopropylphenyl)-N-isopropylformamide and 1-adamantyloxytrimethylsilane. $^1H$ NMR (300 MHz, $CDCl_3$) δ 11.39 (s, 1H), 7.52-7.36 (m, 1H), 7.33-7.19 (m, 2H), 5.01-4.88 (m, 1H), 2.77-2.61 (m, 2H), 2.31-2.22 (m, 9H), 1.79-1.58 (m, 6H), 1.54 (d, J=6.8 Hz, 6H), 1.29 (d, J=6.8 Hz, 6H), 1.11 (d, J=6.8 Hz, 6H); $^{13}C$ NMR (75 MHz, $CDCl_3$) δ 169.4, 144.5, 131.0, 130.0, 125.2, 94.7, 60.3, 42.1, 35.1, 31.8, 29.3, 25.7, 23.3, 22.4. HRMS-ESI (m/z): [M−Cl]$^+$ calcd for $C_{26}H_{40}NO$, 382.3110; found, 382.3108.

2,6-Diisopropylphenoxy-N-cyclohexyl-N-(2,6-diisopropylphenyl)methanaminium chloride (1d). With the same method used in the synthesis of 1a, 1d (42.4%) was obtained as a white solid from N-(2,6-diisopropylphenyl)-N-cyclohexylformamide and 2,6-diisopropylphenoxytrimethylsilane. $^1$H NMR (300 MHz, CDCl$_3$) δ 10.26 (s, 1H), 7.56-7.48 (m, 1H), 7.40-7.34 (m, 2H), 7.33-7.27 (m, 1H), 7.22-7.14 (m, 2H), 4.25-4.12 (m, 1H), 3.13-3.00 (m, 2H), 2.92-2.79 (m, 2H), 2.48-2.36 (m, 2H), 2.01-1.89 (m, 2H), 1.87-1.64 (m, 3H), 1.46-1.17 (m, 27H); $^{13}$C NMR (300 MHz, CDCl$_3$) 169.0, 149.2, 144.5, 138.7, 131.4, 129.1, 125.8, 125.4, 123.6, 68.1, 32.3, 29.4, 27.5, 25.7, 25.0, 24.8, 23.0. HRMS-APCI (m/z): [M−Cl]$^+$ calcd for C$_{31}$H$_{46}$NO, 448.3574; found, 448.3580.

2,6-Diisopropylphenoxy-N-(1-adamantyl)-N-(2,6-dimethylphenyl)methanaminium chloride (1e). With the same method used in the synthesis of 1a, 1e (67.8%) was obtained as a white solid from N-(2,6-dimethylphenyl)-N-(1-adamantyl)formamide and 2,6-diisopropylphenoxytrimethylsilane. $^1$H NMR (300 MHz, CDCl$_3$) δ 11.84 (s, 1H), 7.34-7.19 (m, 4H), 7.18-7.07 (m, 2H), 3.01-2.70 (m, 2H), 2.43 (s, 12H), 2.24 (br. s, 3H), 1.89-1.77 (m, 3H), 1.69-1.57 (m, 3H), 1.21 (d, J=6.7 Hz, 12H); $^{13}$C NMR (300 MHz, CDCl$_3$) δ 172.5, 149.3, 138.5, 133.9, 133.4, 130.2, 129.9, 129.1, 124.8, 70.0, 42.4, 35.1, 30.8, 27.8, 23.4, 20.0. HRMS-ESI (m/z): [M−Cl]$^+$ calcd for C$_{31}$H$_{42}$NO, 444.3266; found, 444.3276.

[N-Diisopropyl-O-(1-adamantyl)aminooxycarbene]gold(I) chloride (2a). To a suspension of 1a (60.2 mg, 0.201 mmol) in THF (2 mL) was added LiHMDS (1.0 M solution in THF) (0.22 mL, 0.22 mmol) at −78° C. After stirring the reaction mixture at the same temperature for 15 min, Me$_2$S.AuCl (64.8 mg, 0.220 mmol) was added. The mixture was stirred at 0° C. for 1 h. Column chromatography (silica gel, 5:1 hexanes/EtOAc) gave 2a (65.1 mg, 32.4%) as an off-white solid. $^1$H NMR (300 MHz, CDCl$_3$) δ 5.62-5.44 (m, 1H), 3.73-3.54 (m, 1H), 2.56-2.40 (m, 4H), 2.35-2.20 (br. s, 2H), 1.81-1.64 (br. s, 5H), 1.63-1.47 (br. s, 3H), 1.38 (d, J=6.8 Hz, 6H), 1.28 (d, J=6.8 Hz, 6H), 0.96-0.75 (m, 1H); $^{13}$C NMR (300 MHz, CDCl$_3$) δ 203.2, 86.0, 48.9, 43.5, 36.0, 31.4, 29.9, 21.1, 20.6. HRMS-DIP-CI (m/z): [M+H]$^+$ calcd for C$_{17}$H$_{30}$AuClNO, 496.1682; found, 496.1666.

[N-(1-Adamantyl)-N-phenyl-O-(1-adamantyl)aminooxycarbene]gold(I) chloride (2b). With the same method used in the synthesis of 2a, 2b (60.5%) was obtained as an off-white solid. $^1$H NMR (300 MHz, CDCl$_3$) δ 7.45-7.28 (m, 3H), 7.20-7.02 (m, 2H), 2.55 (d, J=2.8 Hz, 6H), 2.27 (br. s, 3H), 2.07 (s, 9H), 1.70 (br. s, 6H), 1.62 (br. s, 6H); $^{13}$C NMR (300 MHz, CDCl$_3$) δ 207.8, 143.7, 129.7, 129.2, 128.9, 87.8, 65.0, 43.3, 41.6, 36.2, 36.0, 31.4, 30.4. HRMS-DIP-CI (m/z): [M−Cl]$^+$ calcd for C$_{27}$H$_{35}$AuNO, 586.2384; found, 586.2365.

[N-(2,6-Diisopropylphenyl)-N-isopropyl-O-(1-adamantyl)aminooxycarbene]gold(I) chloride (2c). With the same method used in the synthesis of 2a, 2c (68.3%) was obtained as an off-white solid. $^1$H NMR (300 MHz, CDCl$_3$) δ 7.34-7.22 (m, 1H), 7.17 (d, J=7.9 Hz, 2H), 5.16-5.02 (m, 1H), 2.76-2.63 (m, 2H), 2.27 (br. s, 6H), 2.16 (br. s, 3H), 1.60 (br. s, 6H), 1.35 (dd, J=0.9, 6.7 Hz, 6H), 1.25 (d, J=6.7 Hz, 6H), 1.11 (d, J=6.7 Hz, 6H); $^{13}$C NMR (300 MHz, CDCl$_3$) δ 207.3, 144.6, 134.6, 129.2, 124.4, 86.8, 59.8, 43.3, 35.9, 31.3, 29.1, 25.9, 23.8, 22.9. HRMS-ESI (m/z): [M+Na]$^+$ calcd for C$_{26}$H$_{39}$AuClNNaO, 636.2283; found, 636.2275.

[N-Cyclohexyl-N-(2,6-diisopropylphenyl)-O-(2,6-diisopropylphenyl)aminooxycarbene]gold(I) chloride (2d). With the same method used in the synthesis of 2a, 2d (72.0%) was obtained as an off-white solid. $^1$H NMR (300 MHz, CDCl$_3$) δ 7.44-7.33 (m, 1H), 7.32-7.18 (m, 3H), 7.17-7.05 (m, 2H), 3.72-3.58 (m, 1H), 3.12-3.00 (m, 2H), 2.94-2.81 (m, 2H), 2.67-2.51 (m, 2H), 2.48-2.34 (m, 2H), 1.99-1.78 (m, 2H), 1.65 (br. s, 1H), 1.45 (d, J=6.8 Hz, 6H), 1.38-1.15 (m, 15H), 1.05 (d, J=6.8 Hz, 6H); $^{13}$C NMR (300 MHz, CDCl$_3$) δ 214.5, 152.1, 143.9, 140.4, 137.8, 129.7, 127.9, 125.4, 125.1, 69.8, 34.5, 29.7, 26.8, 26.6, 26.2, 25.4, 25.1, 24.7, 24.6. HRMS-ESI (m/z): [M+Na]$^+$ calcd for C$_{31}$H$_{45}$AuClNNaO, 702.2753; found, 702.2747.

[N-(1-Adamantyl-N-(2,6-dimethylphenyl)-O-(2,6-diisopropylphenyl)aminooxycarbene]gold(I) chloride (2e). With the same method used in the synthesis of 2a, 2e (80.8%) was obtained as an off-white solid. $^1$H NMR (300 MHz, CDCl$_3$) δ 7.22-6.96 (m, 6H), 3.01-2.85 (m, 2H), 2.64 (br. s, 6H), 2.39 (s, 6H), 2.18 (br. s, 3H), 1.77-1.61 (m, 6H), 1.35 (d, J=6.8 Hz, 6H), 0.94 (d, J=7.1 Hz, 6H); $^{13}$C NMR (300 MHz, CDCl$_3$) δ 214.7, 152.3, 139.9, 139.0, 134.0, 129.0, 128.4, 127.6, 124.4, 66.4, 44.1, 36.0, 30.8, 27.4, 24.0, 23.0, 20.6. HRMS-ESI (m/z): [M+Na]$^+$ calcd for C$_{31}$H$_{41}$AuClNNaO, 698.2440; found, 698.2442.

Au(I)-Catalyzed Intramolecular Hydroamination of Alkenyl Ureas Reactions for FIG. 2.3, A mixture of a gold-chloride complex (5.0 μmol) and AgOTf (5.0 μmol) in 1,4-dioxane (2.0 mL) was stirred for 30 min before adding N-(2,2-Diphenyl-4-pentenyl)-N'-phenylurea (3a)[16b] (0.100 mmol). After stirring the reaction mixture for a specified time at room temperature, an aliquot (0.3 mL) of the reaction solution was taken and filtered. After evaporation of the solvent in vacuo, the conversion was calculated by $^1$H NMR comparing the integration of the reactant (3a) and the product (4a)[16b]. The regioselectivity was calculated by $^1$H NMR[16b].

References, Each Of Which Is Incorporated Herein By Reference 1. (a) Jahnke, M. C.; Hahn, F. E. *Top. Organomet. Chem.* 2010, 30, 95. (b) Vougioukalakis, G. C.; Grubbs, R. H. *Chem. Rev.* 2010, 110, 1746. (c) Nolan, S. P. *Acc. Chem. Res.* 2010, 44, 91. (d) Diez-González, S.; Marion, N.; Nolan, S. P. *Chem. Rev.* 2009, 109, 3612. (e) Glorius, F. *Top. Organomet. Chem.* 2007, 21, 1.
2. Recent examples of CAOCs; (a) Yu, I.; Wallis, C. J.; Patrick, B. O.; Diaconescu, P. L.; Mehrkhodavandi, P. *Organometallics* 2010, 29, 6065. (b) Bellemin-Laponnaz, S. *Polyhedron* 2010, 29, 30. (c) Lindner, R.; Wagner, C.; Steinborn, D. *J. Am. Chem. Soc.* 2009, 131, 8861. (d) Cabeza, J. A.; del Rio, I.; Miguel, D.; Pérez-Carreño, E.; Sánchez-Vega, M. G. *Organometallics* 2008, 27, 211. (e) Cabeza, J. A.; del Rio, I.; Miguel, D.; Pérez-Carreño, E.; Sánchez-Vega, M. G. *Dalton Trans.* 2008, 1937. (f) Ruiz, J.; Perandones, B. F.; Garcia, G.; Mosquera, M. E. G. *Organometallics* 2007, 26, 5687. (g) Ruiz, J.; Garcia, G.; Mosquera, M. E. G.; Perandones, B. F.; Gonzalo, M. P.; Vivanco, M. *J. Am. Chem. Soc.* 2005, 127, 8584. (h) Hahn, F. E.; Hein, P.; Lügger, T. Z. *Anorg. Allg. Chem.* 2003, 629, 1316. (i) Couture, P.; Warkentin, J. *Can. J. Chem.* 1997, 75, 1281 and references therein.
3. To the best of the authors' knowledge, there is only one example of metal-CAOC catalyzed reaction; Tubaro, C.; Biffis, A.; Basato, M.; Benetollo, F.; Cavell, K. J.; Ooi, L.-L. *Organometallics* 2005, 24, 4153.
4. (a) Würtz, S.; Glorius, F. *Acc. Chem. Res.* 2008, 41, 1523. (b) Kantchev, E. A. B.; O'Brien, C. J.; Organ, M. G. *Angew. Chem., Int. Ed.* 2007, 46, 2768. (c) Scott, N. M.; Nolan, S. P. *Eur. J. Inorg. Chem.* 2005, 1815.
5. (a) Lentz, D.; Marschall, R. *Chem. Ber.* 1990, 123, 751. (b) Wada, M.; Kanai, S.-I.; Maeda, R.; Kinoshita, M.; Oguro, K. *Inorg. Chem.* 1979, 18, 417. (c) Parks, J. E.; Balch, A. L. *J. Organomet. Chem.* 1974, 71, 453. (d) Minghetti, G.; Bonati, F. *J. Organomet. Chem.* 1973, 54, C62. (e) Bonati, F.; Minghetti, G. *J. Organomet. Chem.*

1970, 24, 251. (f) Crociani, B.; Boschi, T.; Belluco, U. *Inorg. Chem.* 1970, 9, 2021. (g) Badley, E. M.; Chatt, J.; Richards, R. L.; Sim, G. A. *J. Chem. Soc., Chem. Commun.* 1969, 1322.
6. (a) Fischer, H.; Reindl, D.; Hofmann, J.; Troll, C. *J. Organomet. Chem.* 1994, 472, 163. (b) Huang, L.; Ozawa, F.; Osakada, K.; Yamamoto, A. *Organometallics* 1989, 8, 2065. (c) Filippou, A. C.; Fischer, E. O.; Müller, G.; Alt, H. G. *J. Organomet. Chem.* 1987, 329, 223. (d) Fisher, E. O.; Kreiβl, F. R.; Winkler, E.; Kreiter, C. G. *Chem. Ber.* 1972, 105, 588. (e) Fischer, E. O.; Kollmeier, H. J. *Angew. Chem., Int. Ed.* 1970, 9, 309. (f) Schöllkopf, U.; Gerhart, F. *Angew. Chem., Int. Ed.* 1967, 6, 560.
7. Metal-CO route allows for introduction of bulky secondary amines, but the available electrophiles for oxygen atom are limited. Bulky alcohols can be introduced by metal-isocyanide route, but nitrogen atom can have only one substituent.
8. Alder, R. W.; Butts, C. P.; Orpen, A. G. *J. Am. Chem. Soc.* 1998, 120, 11526.
9. (a) Conejero, S.; Canac, Y.; Tham, F. S.; Bertrand, G. *Angew. Chem., Int. Ed.* 2004, 43, 4089. (b) Merceron-Saffon, N.; Baceiredo, A.; Gornitzka, H.; Bertrand, G. *Science* 2003, 301, 1223.
10. (a) Eberhard, M. R.; van Vilet, B.; Pachon, L. D.; Rothenberg, G.; Eastham, G.; Kooijman, H.; Spek, A. L.; Elsevier, C. J. *Eur. J. Inorg. Chem.* 2009, 1313. (b) Kremzow, D.; Seidel, G.; Lehmann, C. W.; Fürstner, A. *Chem.-Eur. J.* 2005, 11, 1833.
11. (a) Seo, H.; Roberts, B. P.; Abboud, K. A.; Merz, Jr. K. M.; Hong, S. *Org. Lett.* 2010, 12, 4860. (b) Snead, D. R.; Inagaki, S.; Abboud, K. A.; Hong, S. *Organometallics* 2010, 29, 1729. (c) Snead, D. R.; Ghiviriga, I.; Abboud, K. A.; Hong, S. *Org. Lett.* 2009, 11, 3274. (d) Hirsch-Weil, D.; Snead, D. R.; Inagaki, S.; Seo, H.; Abboud, K. A.; Hong, S. *Chem. Commun.* 2009, 2475.
12. Poater, A.; Cosenza, B.; Correa, A.; Giudice, S.; Ragone, F.; Scarano, V.; Cavallo, L. *Eur. J. Inorg. Chem.* 2009, 1759; see the Supporting Information for detailed calculations
13. (a) Structures in FIG. 2.2 were drawn using OLEX2 program; Dolomanov, O. V.; Bourhis, L. J.; Gildea, R. J.; Howard, J. A. K.; Puschmann, H. *J. Appl. Cryst.* 2009, 42, 339.
14. IPr=1,3-bis(2,6-diisopropylphenyl)imidazol-2-ylidene
15. (a) Hashmi, A. S. K.; Häffner, T.; Rudolph, M.; Rominger, F. *Eur. J. Org. Chem.* 2011, 667. (b) Hashmi, A. S. K.; Bührle, M.; Wölfle, M.; Rudolph, M.; Wieteck, M.; Rominger, F.; Frey, W. *Chem.-Eur. J.* 2010, 16, 9846. (c) Hashmi, A. S. K.; Hengst, T.; Lothschütz, C.; Rominger, F. *Adv. Synth. Catal.* 2010, 352, 1315. (d) Bartolomé, C.; Garcia-Cuadrado, D.; Ramiro, Z.; Espinet, P. *Inorg. Chem.* 2010, 49, 9758. (e) Bartolomé, C.; Garcia-Cuadrado, D.; Ramiro, Z.; Espinet, P. *Organometallics* 2010, 29, 3589. (f) Bartolomé, C.; Ramiro, Z.; Garcia-Cuadrado, D.; Pérez-Galán, P.; Raducan, M.; Bour, C.; Echavarren, A. M.; Espinet, P. *Organometallics* 2010, 29, 951. (g) Bartolomé, C.; Ramiro, Z.; Pérez-Galán, P.; Bour, C.; Raducan, M.; Echavarren, A. M.; Espinet, P. *Inorg. Chem.* 2008, 47, 11391.
16. (a) Bender, C. F.; Widenhoefer, R. A. *Chem. Commun.* 2008, 2741. (b) Bender, C. F.; Widenhoefer, R. A. *Org. Lett.* 2006, 8, 5303. (c) Bender, C. F.; Widenhoefer, R. A. *Chem. Commun.* 2006, 4143. (d) Han, X.; Widenhoefer, R. A. *Angew. Chem., Int. Ed.* 2006, 45, 1747.
17. See the Supporting Information for more details
18. When IPrAuCl was used as a catalyst, 92% yield with 3.6:1 cis:trans ratio was observed for the formation of 4e, and 99% yield with 2.9:1 cis:trans ratio for the formation of 4f. See reference 16b.

Example 2

All reactions were conducted in flame-dried glassware under an inert atmosphere of dry argon. THF, $CH_2Cl_2$, and toluene were purified under a positive pressure of dry nitrogen by Meyer Solvent Dispensing System prior to use. 1,4-Dioxane was dried over Na/benzophenone and was distilled. All the other chemicals used were purchased from Sigma-Aldrich Co., Acros Organics and Strem Chemicals Inc. and were used as received without further purification. NMR spectra were recorded using a Mercury-300 FT-NMR, operating at 300 MHz for $^1H$ NMR and at 75.4 MHz for $^{13}C$ NMR. All chemical shifts for $^1H$ and $^{13}C$ NMR spectroscopy were referenced to residual signals from $CDCl_3$ ($^1H$) 7.27 ppm, ($^{13}C$) 77.23 ppm. High resolution mass spectra were recorded on a Finnigan MAT95Q Hybrid Sector spectrometer or an Agilent 6210 TOF-LC/MS.

Experimental Details

N-(1-adamantyl)-2,6-dimethylanline (S1)[1] 1-Adamantyloxytrimethylsilane (S2)[2], 2,6-diisopropylphenoxytrimethylsilane (S3)[3], N-(1-adamantyl)-N-phenylformamide (S4)[4] were synthesized by published methods.

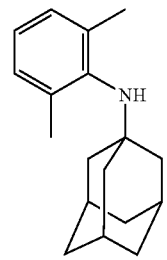

S1

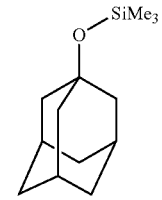

S2

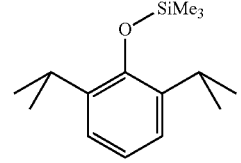

S3

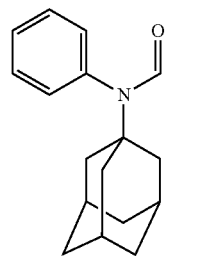

S4

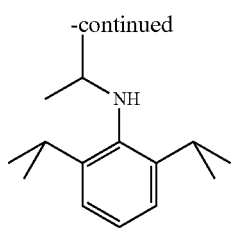

N-Isopropyl-2,6-diisopropylaniline (S5). NaBH(OAc)₃ (3.2 g, 15 mmol) was added into a solution of 2,6-diisopropylaniline (0.940 mL, 4.98 mmol), acetone (1.8 mL, 25 mmol) and acetic acid (0.57 mL, 10 mmol) in 1,2-dichloroethane (30 mL) at room temperature. After stirring at room temperature for 16 h, the reaction was quenched by adding 1M NaOH aq. solution (20 mL). The organic layer was extracted with CH₂Cl₂ (30 mL), and the volatiles were evaporated under reduced pressure. Column chromatography (silica gel, 20:1 hexane/ethyl acetate) gave the product (0.733 g, 66.8%). $^1$H NMR (300 MHz, CDCl₃) δ 7.24-6.95 (m, 3H), 3.47-3.12 (m, 3H), 2.86 (br. s, 1H), 1.27 (d, J=7.0 Hz, 12H), 1.19 (d, J=6.4 Hz, 6H); $^{13}$C NMR (75 MHz, CDCl₃) δ 142.4, 142.1, 123.6, 123.3, 51.6, 28.0, 24.5, 23.7. HRMS-ESI (m/z): [M+H]⁺ calcd for C₁₅H₂₆N, 220.2065; found, 220.2064.

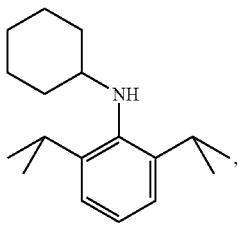 [SMILES: CC(C)c1cccc(C(C)C)c1NC1CCCCC1]

N-Cyclohexyl-2,6-diisoproylaniline (S6). With the same method used in the synthesis of S5, S6 (34.7%) was obtained. $^1$H NMR (300 MHz, CDCl₃) δ 7.17-7.10 (m, 2H), 7.08-7.01 (m, 1H), 3.36-3.27 (m, 2H), 2.97 (br. s, 1H), 2.85-2.77 (m, 1H), 2.08-1.99 (m, 2H), 1.84-1.76 (m, 2H), 1.71-1.62 (m, 1H), 1.28 (d, J=6.8 Hz, 12H), 1.26-1.13 (m, 5H); $^{13}$C NMR (75 MHz, CDCl₃) δ 142.1, 142.0, 123.6, 123.1, 59.7, 34.9, 28.1, 26.3, 26.2, 24.5. HRMS-DART (m/z): [M+H]⁺ calcd for C₁₈H₃₀N, 260.2378; found, 260.2383.

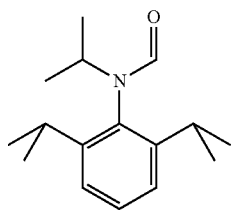 [SMILES: CC(C)c1cccc(C(C)C)c1N(C=O)C(C)C]

N-(2,6-Diisopropylphenyl)-N-isopropylformamide (S7). Acetic formic anhydride (0.63 mL, 8.0 mmol) was added in a solution of S5 (1.043 g, 4.75 mmol) in THF (10 mL). The solution was stirred at 40° C. for 7 h. An aqueous solution of NaOH (1.0 M, 20 mL) was added, and the organic phase was extracted with Et₂O (30 mL×2). After evaporation of the solvents, column chromatography (silicagel, 4:1 hexane:EtOAc) afforded approximately a 4:1 isomeric mixture of the formamide (1.075 g, 91.6%). $^1$H NMR (300 MHz, CDCl₃) δ 8.62 (s, 0.2H), 8.04 (s, 0.8H), 7.38-7.27 (m, 1H), 7.20 (d, J=7.7 Hz, 2H), 4.34-4.18 (m, 0.8H), 3.74-3.62 (m, 0.2H), 3.14-2.97 (m, 1.6H), 2.96-2.86 (m, 0.4H), 1.41 (d, J=6.8 Hz, 1.2H), 1.30-1.08 (m, 16.8H); $^{13}$C NMR (75 MHz, CDCl₃) δ 163.8, 162.2, 148.7, 146.6, 134.9, 129.5, 128.8, 124.4, 124.3, 49.5, 29.1, 28.8, 25.7, 25.3, 23.8, 23.4, 23.0, 20.9. HRMS-DART (m/z): [M+H]⁺ calcd for C₁₆H₂₆NO, 248.2014; found, 248.2009.

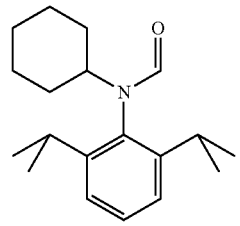 [SMILES: CC(C)c1cccc(C(C)C)c1N(C=O)C1CCCCC1]

N-(2,6-Diisopropylphenyl)-N-cyclohexylformamide (S8). Acetic formic anhydride (0.39 mL, 5.0 mmol) was added in solution of S6 (0.832 g, 3.21 mmol) in THF (10 mL). The solution was stirred at 50° C. for 7 h. An aqueous solution of NaOH (1.0 M, 20 mL) was added, and the organic phase was extracted with Et₂O (30 mL×2). After evaporation of the solvents, column chromatography (silica gel, 4:1 hexane:EtOAc) afforded approximately a 10:1 isomeric mixture of the product (0.715 g, 77.6%). $^1$H NMR (300 MHz, CDCl₃) of the major product δ 8.02 (s, 1H), 7.35-7.26 (m, 1H), 7.21-7.13 (m, 2H), 3.95-3.83 (m, 1H), 3.14-2.99 (m, 2H), 2.08-1.95 (m, 2H), 1.80-1.54 (m, 4H), 1.33-1.19 (m, 10H), 1.12-1.05 (m, 6H); $^{13}$C NMR (75 MHz, CDCl₃) of the isomeric mixture δ 163.7, 162.0, 148.7, 146.5, 134.8, 129.4, 128.7, 124.4, 124.2, 62.0, 57.9, 33.6, 31.0, 29.1, 28.7, 26.4, 26.1, 26.0, 25.7, 25.6, 25.3, 23.9, 23.5. HRMS-DART (m/z): [M+H]⁺ calcd for C₁₉H₃₀NO, 288.2327; found, 288.2318.

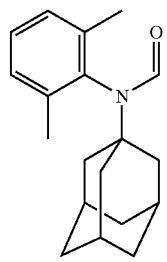 [SMILES: Cc1cccc(C)c1N(C=O)C12CC3CC(CC(C3)C1)C2]

N-(2,6-Dimethylphenyl)-N-(1-adamantyl)formamide (S9). Acetic formic anhydride (2.0 mL, 25 mmol) and S1 (0.320 g, 1.25 mmol) was mixed and heated at 90° C. for 12 h. After cooling to room temperature, An aqueous solution of NaOH (1.0 M, 40 mL) was added, and the organic phase was extracted with Et₂O (30 mL×2). After evaporation of the solvents, column chromatography (silica gel, 4:1 hexane:EtOAc) afforded approximately a 1:1 isomeric mixture of the product (0.192 g, 54.1%). $^1$H NMR (300 MHz, CDCl₃) δ 8.75 (s, 0.5H), 7.97 (s, 0.5H), 7.15-7.04 (m, 3H), 2.34 (s, 3H), 2.26 (s, 3H), 2.21-2.16 (m, 3H), 2.15-2.10 (m, 1.5H), 2.09-2.03 (m, 1.5H), 2.02-1.97 (m, 3H), 1.75-1.60 (m, 6H); $^{13}$C NMR (75 MHz, CDCl₃) δ 163.9, 162.0, 138.7, 137.0, 128.7, 128.2, 127.8, 59.9, 58.0, 44.0, 40.4, 36.6, 36.2, 30.3, 30.2, 20.7, 20.5. HRMS-ESI (m/z): [M+H]⁺ calcd for C₁₉H₂₆NO, 284.2014; found, 284.1999.

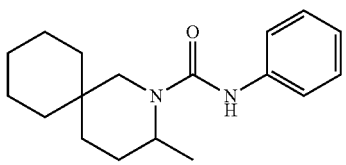 [SMILES: CC1CCC2(CCCCC2)CN1C(=O)Nc1ccccc1]

3-Methyl-N-phenyl-2-azaspiro[5.5]undecane-2-carboxamide (4c). A mixture of 2e (5 mol %) and AgOTf (5 mol %) in MeOH (2.0 mL) was stirred for 30 min before adding 3c (28.7 mg, 0.100 mmol). After stirring the reaction mixture for 48 h at room temperature, the solvent was evaporated. Column chromatography (silica gel, 5:1 hexane:EtOAc) gave the desired product (27.0 mg, 94%). $^1$H NMR (300 MHz, CDCl$_3$) δ 7.40-7.36 (m, 2H), 7.34-7.26 (m, 2H), 7.03 (m, 1H), 6.34 (br. s, 1H), 4.40-4.28 (m, 1H), 3.81 (d, J=14.0 Hz, 1H), 2.70 (d, J=13.6 Hz, 1H), 2.02-1.89 (m, 1H), 1.55-1.27 (m, 13H), 1.24 (d, J=6.9 Hz, 3H); $^{13}$C NMR (300 MHz, CDCl$_3$) δ 155.3, 139.6, 129.0, 123.0, 120.0, 47.1, 38.2, 33.6, 31.8, 26.8, 26.0, 22.1, 21.7, 16.3. HRMS-ESI (m/z): [M+Na]$^+$ calcd for C$_{18}$H$_{26}$N$_2$NaO, 309.1943; found, 309.1951.

References, Each Of Which Is Incorporated Herein By Reference

1. Ehrentraut, A.; Zapf, A.; Beller, M. *J. Mol. Catal. A: Chem.* 2002, 182, 515.
2. Sasaki, T.; Nakanishi, A.; Ohno, M. *J. Org. Chem.* 1982, 47, 3219.
3. Arney, D. J.; Wexler, P. A.; Wigley, D. E. *Organometallics* 1990, 9, 1282.
4. Seo, H.; Roberts, B. P.; Abboud, K. A.; Merz, Jr. K. M.; Hong, S. *Org. Lett.* 2010, 12, 4860.
5. SHELXTL6 (2000). Bruker-AXS, Madison, Wis., USA.
6. van der Sluis, P.; Spek, A. L. *Acta Cryst. A,* 1990, 46, 194.
7. Spek, A. L. *Acta Cryst. A,* 1990, 46, C34.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measuring technique and the numerical value. In addition, the phrase "about 'x' to 'y'" includes "about 'x' to about 'y'".

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

We claim at least the following:

1. A compound, comprising a formula of compound A:

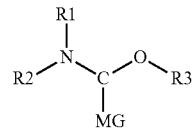

wherein MG is a metal group, and wherein R1, R2, and R3 are each independently selected from a group consisting of: tert-butyl, adamantyl, isopropyl, cyclopentyl, cyclohexyl, cycloheptyl, cyclooctyl, 1-phenylethyl, 1-cyclohexylethyl, 1-(1-naphthyl)ethyl, 1-(tert-butyl)ethyl, 1-(o-methoxyphenyl)ethyl, phenyl (Ph), 2,6-diisopropylphenyl, 2,6-dimethylphenyl, 1-naphthyl, 2-naphthyl, 2-alkylphenyl, 2-alkoxyphenyl, 2-halophenyl, 2-arylphenyl, 4-alkylphenyl, 4-alkoxyphenyl, 4-halophenyl, 4-arylphenyl, 3,5-dialkylphenyl, 3,5-dialkoxyphenyl, 3,5-dihalophenyl, and 3,5-diarylphenyl, any of which is unsubstituted or substituted.

2. The compound of claim 1, wherein the metal of the metal group is selected from the group consisting of: Au, Pt, Ir, Rh, Re, Ru, Ni, Pd, Cu, Fe, and Co.

3. The compound of claim 1, wherein MG is AuCl.

4. A compound, comprising a formula of compound A:

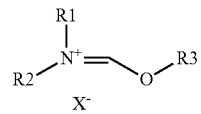

wherein R1, R2, and R3 are each independently selected from a group consisting of: an unsubstituted or substituted alkyl group, an unsubstituted or substituted cycloalkyl group, and an unsubstituted or substituted aryl group, and X is selected from Cl, Br, I, BF$_4$, PF$_6$, BAr$_4$, ClO$_4$, OAc, OTf, Ts, Ms, NTf$_2$, and PO$_2$Cl$_2$.

5. The compound of claim 4, wherein R1, R2, and R3 are each independently selected from tert-butyl, adamantyl, isopropyl, cyclopentyl, cyclohexyl, cycloheptyl, cyclooctyl, 1-phenylethyl, 1-cyclohexylethyl, 1-(1-naphthyl)ethyl, 1-(tert-butyl)ethyl, 1-(o-methoxyphenyl)ethyl, phenyl (Ph), 2,6-diisopropylphenyl, 2,6-dimethylphenyl, 1-naphthyl, 2-naphthyl, 2-alkylphenyl, 2-alkoxyphenyl, 2-halophenyl, 2-arylphenyl, 4alkylphenyl, 4-alkoxyphenyl, 4-halophenyl, 4-arylphenyl, 3,5-dialkylphenyl, 3,5-dialkoxyphenyl, 3,5-dihalophenyl, and 3,5-diarylphenyl, any of which can be unsubstituted or substituted.

6. The compound of claim 4, wherein R1, R2, and R3 are each independently selected from adamantyl, isopropyl, cyclohexyl, phenyl, 2,6-diisopropylphenyl, and 2,6-dimethylphenyl.

7. The compound of claim 4, wherein R1, R2, and R3 are each is independently selected from the group consisting of: adamantyl, isopropyl, cyclohexyl, phenyl, 2,6-diisopropylphenyl, and 2,6-dimethylphenyl.

8. The compound of claim 4, wherein R1, R2, and R3 are each is independently selected from the group consisting of: an unsubstituted or substituted phenyl group, an unsubstituted or substituted cyclohexyl group, and adamantly group.

9. A compound, comprising a formula of compound A:

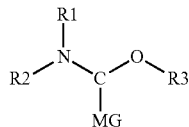

wherein R1, R2, and R3 are each independently selected from the group consisting of:
  adamantyl, isopropyl, cyclohexyl, phenyl, 2,6-diisopropylphenyl, and 2,6-dimethylphenyl; and MG is a metal group.

10. The compound of claim 9, wherein the metal of the metal group is selected from the group consisting of: Au, Pt, Ir, Rh, Re, Ru, Ni, Pd, Cu, Fe, and Co.

11. The compound of claim 9, wherein MG is AuCl.

12. A compound, comprising a formula of compound A:

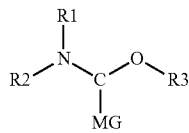

wherein R1, R2, and R3 are each independently selected from the group consisting of: an unsubstituted or substituted phenyl group, an unsubstituted or substituted cyclohexyl group, and adamantly group; and MG is a metal group.

13. The compound of claim 12, wherein the metal of the metal group is selected from the group consisting of: Au, Pt, Ir, Rh, Re, Ru, Ni, Pd, Cu, Fe, and Co.

14. The compound of claim 12, wherein MG is AuCl.

15. A compound, comprising a formula of compound A:

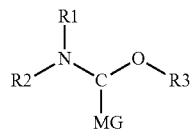

wherein R1, R2, and R3 are each independently selected from a group consisting of: an unsubstituted or substituted alkyl group, an unsubstituted or substituted cycloalkyl group, and an unsubstituted or substituted aryl group; and wherein MG is AuCl.

16. The compound of claim 15, wherein R1, R2, and R3 are each is independently selected from the group consisting of: adamantyl, isopropyl, cyclohexyl, phenyl, 2,6-diisopropylphenyl, and 2,6-dimethylphenyl.

17. The compound of claim 15, wherein R1, R2, and R3 are each independently selected from the group consisting of: an unsubstituted or substituted phenyl group, an unsubstituted or substituted cyclohexyl group, and adamantly group.

18. The compound of claim 15, wherein R1, R2, and R3 are each independently selected from tert-butyl, adamantyl, isopropyl, cyclopentyl, cyclohexyl, cycloheptyl, cyclooctyl, 1-phenylethyl, 1-cyclohexylethyl, 1-(1-naphthyl)ethyl, 1-(tert-butyl)ethyl, 1-(o-methoxyphenyl)ethyl, phenyl (Ph), 2,6-diisopropylphenyl, 2,6-dimethylphenyl, 1-naphthyl, 2-naphthyl, 2-alkylphenyl, 2-alkoxyphenyl, 2-halophenyl, 2-arylphenyl, 4-alkylphenyl, 4-alkoxyphenyl, 4-halophenyl, 4-arylphenyl, 3,5-dialkylphenyl, 3,5-dialkoxyphenyl, 3,5-dihalophenyl, and 3,5-diarylphenyl, any of which can be unsubstituted or substituted.

* * * * *